United States Patent
Palu et al.

(10) Patent No.: US 7,268,162 B2
(45) Date of Patent: Sep. 11, 2007

(54) ALOE-EMODIN DERIVATIVES AND THEIR USE IN THE TREATMENT OF NEOPLASIAS

(75) Inventors: Giorgio Palu, Montegrotto Terme (IT); Modesto Carli, Padova (IT); Teresa Pecere, Padova (IT); Giuseppe Zagotto, Terrossa (IT)

(73) Assignee: Universita' Degli Studi di Padova, Padua (IT)

( * ) Notice: Subject to any disclaimer, the term of this patent is extended or adjusted under 35 U.S.C. 154(b) by 484 days.

(21) Appl. No.: 10/477,347

(22) PCT Filed: May 10, 2002

(86) PCT No.: PCT/IB02/01604

§ 371 (c)(1),
(2), (4) Date: May 17, 2004

(87) PCT Pub. No.: WO02/090313

PCT Pub. Date: Nov. 14, 2002

(65) Prior Publication Data

US 2004/0192623 A1    Sep. 30, 2004

(30) Foreign Application Priority Data

May 10, 2001 (IT) .......................... MI2001A0957

(51) Int. Cl.
*A61K 31/21* (2006.01)
*C07C 50/18* (2006.01)

(52) U.S. Cl. ...................................... 514/510; 552/266

(58) Field of Classification Search ................ 552/266; 514/510
See application file for complete search history.

(56) References Cited

FOREIGN PATENT DOCUMENTS

WO    WO0191735    12/2001

OTHER PUBLICATIONS

Abramson et al., "Synthesis of Anthraquinonyl Glucosaminosides and Studies on the Influence of Aglycone Hydroxyl . . . ", *Journal of Medical Chemistry*, vol. 29, pp. 1709-1714, (1986).
Pecere et al., "Aloe-emodin Is a New Type of Anticancer Agent with Selective Activity Against Neuroectodermal Tumors", *Cancer Research*, vol. 60, pp. 2800-2804, (2000).
Horhammer et al., "Aloinosid B, ein neues Glykosid aus Aloe", *Organische Chemie*, vol. 19, pp. 222-226 (1964).
Connor et al., "Anthracene and Chromone Derivatives in the Exudate of Aloe Rabaiensis", *Phytochemistry*, vol. 28, No. 12, pp. 3551-3553, (1989).
Okabe et al., "Rhubarb (*Rhei rhizoma*).II Anthraquinone glycosides", *Chemical and Pharmaceutical Bulletin*, vol. 21, No. 6, pp. 1254-1260,(1973).
Benfaremo et al., Studies in Anthracycline Synthesis: simple Diels-Alder Routes to Pachybasin, Omega-hydroxypachybasin, aloe-emodin, and fallacinol, *Journal of Organic Chemistry*, vol. 50, No. 1, pp. 139-141 (1985).
Xiuwen et al., "Synthesis and Antitumor Activity of 2,3-bis(acyloxymethyl)-1,4-dihydroxyanthraquinones", *Pharmaceuticals*, vol. 20, No. 8 pp. 343-346 (1989), Abstract only.
Kupchan et al., "Tumor Inhibitors" 114. Aloe Emodin: Antileukemic Principle Isolated from Rhamnus Frangula L, *LLoydia*, vol. 39, No. 4, pp. 223-222 (1976) (Abstract).
Acevedo-Duncan et al., "Aloe-emodin modulates PKC isozymes, inhibits proliferation, and induces apoptosis in U-373 MG Glioma Cells", *International Immunopharmacology 4*, pp. 1775-1784 (2004).

*Primary Examiner*—Barbara P. Badio
(74) *Attorney, Agent, or Firm*—Abelman, Frayne & Schwab

(57) ABSTRACT

The invention relates to aloe-emodin (AE) derivatives and their use as anticancer drugs. Saids derivatives show a specific cytotoxicity to tumour cells, also of neuroectodermal origin, to which they may in particular act as aloe-emodin prodrugs. Said pharamcological profile makes them particularly suitable for use in the treatment of neoplasias. Thereofore, pharmaceutical compositions containing said compound may be usefully used in the treatment of neoplasias. It has surprisingly been found that aloe-emodin derivatives in position 3' (bearing either a positive or negaive charge) exhibit improved sollubility properties and, at the same time, in vitro show cytotoxicity to tumour cells, also of neuroectodermal origin.

27 Claims, No Drawings

ALOE-EMODIN DERIVATIVES AND THEIR USE IN THE TREATMENT OF NEOPLASIAS

This application is a 371 of PCT/IB02/01604 file May 10, 2002.

FIELD OF THE INVENTION

The present invention relates to aloe-emodin (AE) derivatives and their use in the treatment of neoplastic pathologies.

PRIOR ART

As known, the therapeutic strategies adopted for the treatment of neoplasias are essentially aimed at killing all malignant cells both in the primary and metastasised sites. To this end, various therapeutic methods can be used, from surgery to radiation therapy for tumours localised in well definite areas or organs, to chemotherapy for local or systemic tumours, to endocrinotherapy for hormone-dependent tumours, to immunotherapy and thermotherapy. To obtain an efficacious therapy for tumour cells eradication, all above methods may be used alone or in combination, depending on the type of tumour cell and on the disease phase.

The most common therapeutic approach is probably chemotherapy either alone or in combination with the aforesaid therapeutic methods. An ideal chemotherapeutic agent should be selective for tumour cells and should not produce serious untoward effects on normal cells as well as systemic toxic effects. However, notwithstanding the considerable research efforts made over the years to identify selective anticancer agents, no compound, used alone or in combination with other compounds, proved to possess a satisfactory therapeutic index, i.e. the ratio of the efficacy on the tumour cell to the absence of cytotoxic effects on non-malignant cells. The anticancer agents known and in clinical use are many and many are the mechanisms at the basis of their cytotoxicity to tumour cells. Alkylating drugs, such as nitrogen mustards, were among the first to be used, followed by antimetabolic drugs, folate-antagonists, such as methotrexate, or purine-antagonists, such as 6-mercaptopurine, or pyrimidine-antagonists, such as 5-fluorouracyl, cell mitosis blockers of vegetable origin, such as vincristine and vinblastine, and podophyllotoxins, antibiotics, such as mitomycins, anthracycline and bleomycins, nitrosoures, platinum coordination compounds and, more recently, the so-called biologic response modifiers, such as the α-interferon and an enzyme, such as asparaginase. All aforesaid drugs are widely used, either alone or in combination, in a wide range of neoplasias, from tumours localised in definite organs to systemic tumours. In the case of tumours of neuroectodermal origin, such as for example neuroblastoma, peripheral primitive neuroectodermal tumour (PNET), Ewing's sarcoma, melanoma, microcytoma, etc., the chemotherapeutic agents usually employed, though non-specific, may be e.g. vincristine and vinblastine, platinum coordination compounds and other compounds right for the purpose.

Notwithstanding the acknowledged efficacy of a number of said compounds, none of them proved to have the aforesaid ideal profile. In fact, an even multiple resistance of tumour cells to said agents was often found, while toxic effects on the other cells were produced.

With a view to identifying compounds capable of selectively acting on tumour cells without inducing serious cytotoxic effects on the other proliferative cells or general toxic effects, the Applicants turned their attention to a natural compound, aloe-emodin, and found that it has a specific cytotoxicity to tumour cells of neuroectodermal origin and does not induce any serious toxic effect (Italian patent application No. MI 2000A001216).

Aloe-emodin (AE) suffers from the disadvantage of being hardly soluble in water and in the physiological solution, while it is soluble only in hot alcohols, ethers, benzene and in water alkalinised by ammonia or acidified by sulphuric acid. Therefore, from the pharmaceutical practice standpoint, said characteristic makes it problematic to use same in the preparation of pharmaceutical products useful for therapeutic treatments.

Abrahamson, H. N. et al. (*J. Med. Chem.* 1986, 29, 1709-1714) describe a derivative of aloe-emodin with glucosamine in order to obtain water soluble model compounds without disclosing however any antitumoral activity of the same.

It is, therefore, an object of the present invention to provide aloe-emodin (AE) derivatives exhibiting an improved solubility, while maintaining the same biological activity as AE and being potential AE pro-drugs.

SUMMARY OF THE INVENTION

It has surprisingly been found that aloe-emodin derivatives in position 3' (bearing either a positive or negative charge) exhibit improved solubility properties and, at the same time, in vitro show cytotoxicity to tumour cells, also of neuroectodermal origin.

It is therefore an object of the present invention to provide aloe-emodin derivatives of formula:

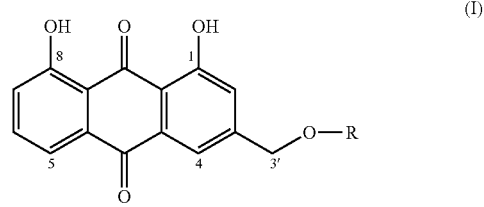

(I)

where R can be the radical of: a saturated or unsaturated $C_2$-$C_6$ linear or branched chain aliphatic polycarboxylic acid, or an arylic polycarboxylic acid or an amino acid or an acetal with an amino sugar or a group of an inorganic acid.

It is a further object of the present invention the use of said aloe-emodin derivatives in pharmaceutical compositions for the treatment of neoplastic pathologies, also of neuroectodermal origin.

It is a still further object of the present invention to provide pharmaceutical compositions containing said derivatives as active ingredients, suitable for the treatment of neoplastic pathologies.

DETAILED DESCRIPTION OF THE INVENTION

The characteristics and advantages of the present invention will be better understood from the following detailed description.

In the aloe-emodin derivatives of formula (I) radical R on the hydroxyl group in position 3' can be:

a saturated or unsaturated aliphatic polycarboxylic acid with a linear or branched chain of from 2 to 6 carbon atoms, also substituted on the aliphatic chain by suitable hydrophilic groups. When R is an aliphatic acid of group a), said acid is preferably selected from one of the following groups: (i) linear saturated aliphatic bicarboxylic acid, e.g. oxalic, malic, succinic, glutaric, adipic, pimelic, diglycolic acids; (ii) or a branched one; (iii) or an unsaturated one, e.g. maleic acid; (iv) or a tricarboxylic acid, e.g. citric acid;

an arylic polycarboxylic acid also substituted on the aromatic ring by small hydrophilic residues, such as for example OH, $CH_2OH$ and equivalents. When R is an aromatic acid of group b) said acid is preferably selected from the group consisting of aromatic systems containing one or more rings, hydrophilic substituents, if any, and at least two carboxylic groups, such as for example phthalic acid and 1,2,4, benzenetricarboxylic acid;

an amino acid (amino group in α- or in other positions), e.g. alanine, isoleucine, tyrosine, tryptophan and GABA;

an acetal with an amino sugar, such as daunosamine and equivalents with the exclusion of glucosamine;

the residue of an inorganic acid, such as for example phosphoric acid and equivalents.

Furthermore, in the derivatives forming the object of the present invention, in which R belongs to groups a) and b), the non-esterified carboxylic groups can be in the free or salified form; in the latter case, pharmaceutically acceptable and known counterions may be used, sodium or potassium being especially preferred. In the derivatives forming the object of the present invention, in which R belongs to groups c) and d), the amine group can be in the free or salified form; in the latter case, pharmaceutically acceptable and known anionic groups may be used, acetate, trifluoroacetate, nitrate, chloride, bromide, acid sulphate being especially preferred.

The following examples and the biological characteristics of compounds synthesized according to the present invention are conveyed by way of indication, not of limitation, of the invention.

EXAMPLE 1

AE Ester with Maleic Anhydride mono-(4,5-dihydroxy-9,10-dioxo-9,10-dihydroanthracen-2-ylmethyl)ester but-2-endioic acid AE (51.7 mg; 270.2 g/mol; 0.19 mmol), maleic anhydride (60.0 mg; 98.1 g/mol; 0.61 mmol) and DMAP (2.7 mg; 122.2 g; 0.022 mmol) were dissolved in anhydrous tetrahydrofuran (5 ml). The reaction was carried out under a stream of nitrogen, with stirring at reflux temperature for 48 hrs. Then the solvent was evaporated under vacuum at room temperature.

The reaction residue was purified by chromatography (eluent: 55% petroleum ether, 45% ethyl acetate).

7 mg of pure compound was obtained. $^1$H-NMR (DMSO$_{d6}$): 5.35 ppm (2H, s, $CH_2$); 6.45 ppm (1H, d, (J=14.8), =CH); 6.55 ppm (1H, d (J=14.8) =CH); 7.43 ppm (2 H, m 7.81 ppm (3H, m, $H^4$, $H^5$, $H^6$); 11.99 and 12.05 ppm (2H, 2 s, 2OH). 368 ($M^+$).

EXAMPLE 2

AE Ester with Succinic Anhydride mono-(4,5-dihydroxy-9,10-dioxo-9,10-dihydroanthracen-2-ylmethyl)ester succinic acid AE (51.7 mg; 0.19 mmol), succinic anhydride (61.0 mg; 0.61 mmol) and DMAP (2.7 mg; 0.022 mmol) were dissolved in anhydrous THF (5 ml). The reaction was carried out under a stream of nitrogen, with stirring at reflux temperature for 48 hrs. The solvent was evaporated under vacuum at room temperature, and the residue was washed three times with ethyl ether. 8.8 mg of pure compound was obtained.

$^1$H-NMR(DMSO$_{d6}$): 5.35 ppm (2H, s, $CH_2$); 2.55 ppm (2H, m, $CH_2^{1'}$); 2.68 ppm (2 H, m, $CH_2^{1''}$); 7.35 ppm (2H, m, $H^2$, $H^7$); 7.77 ppm (3H, m, $H^4$, $H^5$, $H^6$). 370 ($M^+$).

EXAMPLE 3

AE Ester with Diglycolic Anhydride (4,5-Dihydroxy-9,10-dioxo-9,10-dihydroanthracen-2-ylmethoxycarbonylmethoxy) acetic acid AE (50.0 mg; 0.185 mmol), diglycolic anhydride (25.8 mg; 0.22 mmol) and DMAP (2.3 mg; 0.18 mmol) were dissolved in anydrous THF (5 ml). The reaction was carried out under a stream of nitrogen, with stirring at reflux temperature for 12 hrs. The solvent was evaporated under vacuum at room temperature.

The solid residue was dissolved in ethyl acetate and the organic solution was extracted with a potassium bicarbonate aqueous solution. The aqueous solution was slightly acidified with acetic acid and extracted again with ethyl acetate. The organic solution dehydrated with sodium sulphate and the solvent was evaporated under vacuum. 32 mg of pure ester was obtained.

$^1$H-NMR(DMSO$_{d6}$): 5.3 ppm (2H, s, $CH_2$); 4.3 ppm (2H, s, $CH_2^{1'}$); 4.16 ppm (2H, s, $CH_2^{2'}$); 7.43 ppm (2H, m, $H^2$, $H^7$); 7.81 ppm (3H, m, $H^4$, $H^5$, $H^6$); 11.99 ppm (2 H, s (broadened) $OH^1$, $OH^8$). 386 ($M^+$).

EXAMPLE 4

AE Ester with Phthalic Anhydride mono-(4,5-dihydroxy-9,10-dioxo-9,10-dihydroanthracen-2-ylmethyl)ester phthalic acid AE (50.0 mg; 0.185 mmol), phthalic anhydride (32.9 mg; 0.22 mmol) and DMAP (2.3 mg; 0.02 mmol) were dissolved in anhydrous THF (5 ml). The reaction was carried out under a stream of nitrogen, with stirring at reflux temperature for 12 hrs. The solvent was evaporated under vacuum at room temperature. The reaction residue was purified by chromatography (eluent: 40% petroleum ether, 60% ethyl acetate). 9.3 mg di pure product was obtained.

$^1$H-NMR(DMSO$_{d6}$): 5.4 ppm (2H, s, $CH_2$); 7.1-8.0 ppm (9H, m, $H^2$, $H^7$; $H^4$, $H^5$, $H^6$; $H^{2'}$, $H^{3'}$, $H^{4'}$, $H^{5'}$). 418 ($M^+$).

EXAMPLE 5

AE ester with 1,2,4-benzenetricarboxylic anhydride 1-(4,5-dihydroxy-9,10-dioxo-9,10-dihydroanthracen-2-ylmethyl)ester 1,2,4-Benzenetricarboxylic acid AE (50.0 mg; 0.185 mmol), benzenetricarboxylic anhydride (42.7 mg; 0.22 mmol) and DMAP (2.3 mg; 0.02 mmol) were dissolved in anhydrous THF (5 ml). The reaction was carried out under a stream of nitrogen, with stirring at reflux temperature for 12 hrs. The solvent was evaporated under vacuum at room temperature.

The solid residue was dissolved in ethyl acetate and the organic solution was extracted with a potassium bicarbonate aqueous solution. The aqueous solution was slightly acidified with acetic acid and extracted again with ethyl acetate. The organic solution was dehydrated with sodium sulphate and the solvent was evaporated under vacuum. 23 mg of pure ester was obtained.

$^1$H-NMR(DMSO$_{d6}$): 5.47 ppm (2H, s, CH$_2$); 7.39-8.4 ppm (8H, m, H$^2$, H$^7$; H$^4$, H$^5$, H$^6$; H$^{3'}$, H$^{5'}$, H$^{6'}$); 11.95 ppm (2H, s (broadened), OH$^1$, OH$^8$). 462 (M$^+$).

EXAMPLE 6

AE Ester with Tryptophan

AE (50.0 mg; 0,185 mmol), Fmoc-L-tryptophan-OPfp (131.5 mg; 0,22 mmol) and DMAP (22.6 mg; 0.02 mmol) were dissolved in anhydrous THF and refluxed overnight under a stream of nitrogen. The solvent was evaporated at room temperature under vacuum. The ester of protected amino acid was obtained.

The residue was taken up with CH$_2$Cl$_2$ (5 ml) and treated with piperidine (157.5 mg; 0.19 mmol) at room temperature for 1 hr.

The solvent and piperidine were removed under vacuum. The residue was taken up with CH$_2$C$_2$ (1 ml) and precipitated with hexane. The solid was washed twice with hexane (2 ml) and dissolved in ethyl acetate. The organic solution was extracted with a potassium bicarbonate aqueous solution. The aqueous solution was slightly acidified and extracted again with ethyl acetate. The organic solution was dehydrated with magnesium sulphate and the solvent was evaporated under vacuum to obtain 8.5 mg of pure product.

$^1$H-NMR(DMSO$_{d6}$): 5.15 ppm (2H, s, CH$_2$); 3.27 ppm (1H, m, CH$^{1'}$); 4.0 ppm (2H, t, CH2$^{2'}$); 7.05-7.91 ppm (9H, m, H$^2$, H$^7$; H$^4$, H$^5$, H$^6$). 456 (M$^+$).

EXAMPLE 7

AE Ester with Alanine

A solution of AE (100 mg; 0.37 mmol) in N,N-dimethylformamide (10 ml) was added with triethylamine (0.1 ml; 0.74 mmol), DMAP (4.5 mg; 0.037 mol) e Boc-L-Ala-OSu (212 mg; 0.74 mmol). After 16 hrs at 60° C., water was added and a precipitate was obtained. The mixture was filtered and the precipitate was washed with water first and then with cold diethyl ether. 67 mg (41%) of Boc-L-Ala-Aloe-emodin was obtained.

$^1$H-NMR (DMSO$_{d6}$): 11.93 ppm (1H, s, OH phenol); 11.91 ppm (1H, s, OH phenol); 7.82 ppm (1H, t, H$^6$); 7.70 ppm (1H, d, H$^5$); 7.69 ppm (1H, s, H$^4$); 7.39 ppm (1H, d, H$^7$); 7.35 ppm (1H, s, H$^2$); 5.28 ppm (1H, d, CH—O); 5.24 ppm (1H, d, CH—O); 4.13 ppm (1H, m, CH—N); 1.37 ppm (9H, s, C(CH$_3$)$_3$); 1.29 ppm (3H, d, CH$_3$).

Boc-L-Ala-AE (20 mg) was dissolved in a 20 ml centrifuge tube with TFA (2.0 ml) in a 90% aqueous solution and stirred for approx. 1 hr.

The product was precipitated by addition of cold ether (5 ml), separated from the supernatant by centrifuging and washed twice with cold ether.

The powder obtained was dried to give 18 mg (87%) of L-Ala-AE.

$^1$H-NMR: in D$_2$O: 7.53 ppm (1, t, H$^7$); 7.39 ppm (1H, d, H$^5$); 7.33 ppm (1H, s, H$^4$); 7.11 ppm (1H, d, H$^7$); 7.03 ppm (1H, s, H$^2$); 5.16 ppm (2H, s, CH$_2$—O); 4.19 ppm (1H, m, CH—N); 1.53 ppm (3H, d, CH$_3$). 342 (M$^+$).

EXAMPLE 8

AE Ester with Isoleucine

A solution of AE (50 mg; 0.185 mmol) in THF (5 ml) was added with Fmoc-L-Ile-OPfp (211 mg; 0.407 mmol). The solution was refluxed for 48 hrs, the solvent was evaporated, and the residue was purified by chromatography (petroleum ether/ethyl acetate 3:1). 42 mg (37%) of Fmoc-L-Ile-Aloe was isolated as an an orange-coloured powder.

$^1$H-NMR (DMSO$_{d6}$): 11.88 ppm (1H, s, OH phenol); 11.86 ppm (1H, s, OH phenol); 7.89-7.60 ppm (7H, m, H$^6$, H$^5$, H$^4$, H$_\alpha$ Fmoc aromatic protons); 7.39 ppm (1H, d, H$^7$); 7.35 ppm (1H, s, H$^2$); 7.34-7.25(4H, m, H$_\beta$ Fmoc aromatic protons); 5.32 ppm (1H, d, CH—O); 5.22 ppm (1H, d, CH—O); 4.35 ppm (1H, m, CH—N); 4.16-4.05 ppm (3H, m, CH, CH$_2$ of Fmoc); 1.89 ppm (1H, m, CH—CH$_3$); 1.43 ppm (1H, m, H of CH$_2$CH$_3$); 1.26 (1H, m, H of CH$_2$CH$_3$); 0.90 ppm (3H, d, CH—CH$_3$); 0.85 ppm (3H, t, CH$_2$—CH$_3$).

Fmoc-L-Ile-AE (19 mg; 0.0314 mmol) was treated with piperidine (0.05 ml; 0.502 mmol) in dichloromethane (2 ml) for 1 hr. The solvent and piperidine were removed under vacuum. The residue was suspended in n-hexane and centrifuged. Once the supernatant solvent was removed, the solid obtained was treated with HCl in ethanol (2 ml). Solvent evaporation gave L-Ile-AE×HCl (10 mg; 77%).

$^1$H-NMR (methanol$_{d4}$): 11.88 ppm (2H, s, OH phenol); 7.83 ppm (1H, t, H$^6$); 7.75 ppm (1H, s, H$^4$); 7.73 ppm (1H, d, H$^5$); 7.45 ppm (1H, s, H$^2$); 7.41 ppm (1 H, d, H$^7$); 5.40 ppm (2H, s, CH$_2$—O); 4.20 ppm (1H, d, CH—N); 2.19 ppm (1H ,m, CH—CH$_3$); 1.59 ppm (1H, m, H of CH$_2$CH); 1.42 ppm (1, m, H of CH$_2$CH$_3$); 1.09 ppm (3 H, d, CH—CH$_3$); 1.05 ppm (3H, t, CH$_2$—CH$_3$). 383 (M$^+$).

EXAMPLE 9

AE Ester with Tyrosine

A solution of AE (100 mg; 0.37 mmol) in N,N-dimethylformamide (10 ml) was added with triethylamine (0.1 ml; 0.74 mmol), DMAP (4.5 mg; 0.037 mol) and Boc-L-Tyr-OSu (280 mg; 0.74 mmol). After 14 hrs at 60° C., water was added and a precipitate was obtained. The mixture was filtered and the precipitate was washed with water first and then with cold diethyl ether. 77 mg (19%) of Boc-L-Tyr-Aloe-emodin was obtained.

$^1$H-NMR (DMSO$_{d6}$): 11.81 ppm (1H, s, OH phenol); 11.76 ppm (1H, s, OH phenol); 9.01 ppm (1H, s, OH phenolic Tyr); 7.83 ppm (1H, t, H$^6$); 7.74 ppm (1H, d, H$^5$); 7.64 ppm (1H, s, H$^4$); 7.41 ppm (1H, d, H$^7$); 7.35 ppm (1H, s, H$^2$); 7.01 ppm (2H, d, J=8.1 Hz, Harom Tyr); 6.01 ppm (2H, d, J=8.1 Hz, Harom Tyr); 5.28 ppm (1H, d, CH—O); 5.24 ppm (1H, d, CH—O); 4.13 ppm (1H, m, CH—N); 1.37 ppm (9H, s, C(CH$_3$)$_3$).

Boc-L-Tyr-AE (20 mg) was dissolved in a 20 ml centrifuge tube with TFA (2.0 ml) in a 90% aqueous solution and stirred for approx. 1 hr.

The product was precipitated by addition of cold ether (5 ml), separated from the supernatant by centrifuging and washed twice with cold ether.

The powder obtained was dried to give 18 mg (87%) of L-Ala-AE.

$^1$H-NMR: in D$_2$O: 7.50 ppm (1, t, H$^7$); 7.41 ppm (1H, d, H$^5$); 7.32 ppm (1H, s, H$^4$); 7.10 ppm (1H, d, H$^7$); 7.02 ppm (1H, s, H$^2$); 7.05 ppm (2H, d, J=8.1 Hz, Harom Tyr); 6.01 ppm (2H, d, J=8.1 Hz, Harom Tyr); 5.16 ppm (2H, s, CH$_2$—O); 4.19 ppm (1H, m, CH—N). 433 (M$^+$).

EXAMPLE 10

AE Ester with Alanine, Salified by Trifluoroacetic Acid

The compound as per Example 7 (5 mg) was treated with conc. trifluoroacetic acid (200 μl) and diluted with acetone. The ala-aloe-emodin trifluoroacetate was separated, filtered and dried.

EXAMPLE 11

AE Ester with Alanine, Salified by Hydrochloric Acid

The compound as per Example 7 (5 mg) was treated with conc. hydrochloric acid (300 μl) and diluted with acetone. The ala-aloe-emodin hydrochloride was separated, filtered and dried.

EXAMPLE 12

AE Ester with Phosphoric Acid

A solution of AE (50 mg; 0.185 mmol) in THF (5 ml) was added with dibenzyloxyphosphorylchloride (396.69 g/mol, prepared according to a known method, 161 mg; 0.407 mmol). Once the solution was refluxed for 6 hrs, the solvent was evaporated and the residue was purified by chromatography (petroleum ether/ethyl acetate 3:1). The benzyl groups were detached by catalytic hydrogenation on Pd/C at atmospheric pressure in dilute sodium hydroxide. 42 mg (64%) of $PO_3^{2-}$-Aloe-emodin was obtained as an orange-coloured powder. 350 ($M^+$, without the two sodium atoms). NMR $^{31}P$ ($D_2O$)=7.1 ppm.

EXAMPLE 13

AE Acetal with Daunosamine

N,O-di(trifluoroacetyl)daunosaminyl-2-bromide (402.09 g/mol, prepared according to a known method, 160 mg; 0.4 mmol) in dichloromethane (3 ml) was caused to react with an AE solution (50 mg; 0.185 mmol) in anhydrous THF (3 ml) in the presence of mercury oxide, mercury dibromide and molecular sieves. When the reaction was on equilibrium (chromatographically) the salts and molecular sieves were filtered and the solvent was evaporated at a reduced pressure. The protecting group (trifluoroacetate) of the OH and $NH_2$ groups of sugar was eliminated by methanolysis. The product was purified by chromatography on neutral alumina. 8 mg (0.02 mmol; 10%) of chromatographically pure product was obtained.

$^1$H-NMR(DMSO$_{d6}$): 1.15 ppm (3H, d, 6.5 Hz, $CH_3$ dauno); 1.77 ppm (1H, m, $H_2$ dauno); 3.31 ppm (1H, m, $H_3$ dauno); 3.62 (1H, m, $H_4$ dauno); 4.14 ppm (1H, m, $H_5$ dauno); 5.25 ppm (1H, broadened singlet, $H_1$ dauno); 5.35 ppm (2H, s, $CH_2$); 6.45 ppm (1H, d, (J=14.8), =CH); 6.55 ppm (1H, d (J=14.8) =CH); 7.43 ppm (2 H, m); 7.81 ppm (3H, m, $H^4$, $H^5$, $H^6$); 11.99 and 12.05 ppm (2H, 2 s, 2OH). 399 ($M^+$).

In vitro Biological Assays

In vitro cytotoxicity assays were conducted on different tumour cell lines, also of neuroectodermal origin. Purpose of said assays was also to check the compounds cytotoxic action and specificity. The cell lines used were of human origin, in particular:

tumours of neuroectodermal origin: neuroblastoma (IMR-5, SJ-N-KP)

tumours of other origins: colon adenocarcinoma (LoVo 109) and glioblastoma (A172).

The aforesaid cells were assayed with the following compounds:

AM: ester of maleic acid (ex. 1) dissolved in DMSO
AS: ester of succinic acid (ex. 2) dissolved in DMSO
ADG: ester of diglycolic acid (ex. 3) dissolved in DMSO
AF: ester of phthalic acid (ex. 4) dissolved in DMSO
ABT: AE ester with 1,2,4-benzenetricarboxylic acid (ex.5) dissolved in HEPES (N-2-hydroxyethylpiperazine-N'-2 ethane sulphonic acid)
TRIP: tryptophan ester (ex. 6) dissolved in DMSO
ALA-NH2: non-salified alanine ester, with the free amine group (ex. 7) dissolved in DMSO
PJ8: ester of isoleucine hydrochloride (ex. 8) dissolved in DMSO
TIR-NH2: tyrosine non-salified ester (ex. 9) dissolved in DMSO
EM9: alanine ester salified by trifluoroacetic acid (ex.10) dissolved in DMSO
ALA: alanine ester in the form of hydrochloride (ex. 11) dissolved in aqueous solution (HEPES 1M)
ALA-HCl: alanine ester in the form of hydrochloride (ex. 11) dissolved in DMSO
AEP: AE phosphoric ester (ex.12) dissolved in HEPES
AED: AE acetal with daunosamine (ex.13) dissolved in HEPES The cells, cultured according to known methods, were seeded 24 hrs prior to treatment with the various derivatives at a concentration of 1000 cells/100 μl. For molecules dissolved in dimethylsulphoxide, DMSO, the concentration of the initial stock was 200 mM and for molecules dissolved in a HEPES buffer and in the physiological solution was 1 mM. The scalar concentrations for the various aloe-emodin derivatives, to which the cells in exponential phase of growth were exposed for 72 hrs, were as follows: 100 μM, 10 μM, 1 μM, 0.1 μM, 0.01 μM.

For each assay, a control was carried out with the medium alone (RPMI with 10% inactivated fetal bovine serum, FBS, and 1% penicillin/streptomycin).

The effects of the various compounds are expressed as EC50, i.e. the effective concentration allowing the presence of 50% viable cells, in comparison with an untreated control. The cells viability was assessed by the MTT dye assay.

Results

The following table shows the results obtained. The EC50 values (μM) referred to each compound and cell line are given. The compound marked with an asterisk shows the data obtained with cells in a medium with non-inactivated FBS, so as to obtain a larger amount of esterase capable of splitting the ester bond on the AE molecule.

| COMPOUND | SJ-N-KP | IMR5 | LoVo 109 |
|---|---|---|---|
| Ex. 1: AM | 270–280 | 270–280 | 250 |
| Ex. 2: AS | 43 | 40 | 43 |
| Ex. 3: ADG | 10 | 10 | 20 |
| Ex. 4: AF | 300 | 250 | 250 |
| Ex. 4: AF* | 50 | 50 | 50 |
| Ex. 5: ABT | 150 | 160 | 250 |
| Ex. 6: TRIP | 8–9 | 10 | 8–9 |
| Ex. 7: ALA-NH2 | 264 | 300 | n.d. |
| Ex. 8: PJ8 | 9 | 9 | 20 |
| Ex. 9: TIR-NH2 | 96.4 | n.d. | 26 |

-continued

| COMPOUND | SJ-N-KP | IMR5 | LoVo 109 |
|---|---|---|---|
| Ex. 10: EM9 | 6.7 | 6.7 | 5 |
| Ex. 11: ALA | 200 | 200 | 200 |
| Ex. 11: ALA-HCl | 70.6 | 70.6 | n.d. |
| Ex. 12: AEP | 12 | 10 | 20 |
| Ex. 13: AED | 5 | 5 | 10 | n.d.: not determined

The above results clearly show that the compounds in question are cytotoxic to tumour cells, also of neuroectodermal origin, and, in particular, that the compounds according to the present invention are surprisingly active against the tumour cells of adenocarcinoma LoVo 109.

Conversely, they are less active against the cell line of glioblastoma A172 (data not reported).

Furthermore, the above experimental data show that the derivatives in question are aloe-emodin pro-drugs. When tested under experimental conditions envisaging non-inactivated FBS and, therefore, in the presence of esterase capable of splitting the ester bond, they show an up to six times strengthened action.

It follows that they may be advantageously used as chemotherapeutic agents in the treatment of tumours, also of neuroectodermal origin, since they make aloe-emodin available within a short time and in the presence of both inactivated and non-inactivated serum (the latter condition simulating the physiological situation). Aloe-emodin, in fact, was ascertained to exert a noticeable in vitro and in vivo pharmacological effect, specific on said cells, without causing any general toxic effect.

Consequently, aloe-emodin derivatives can be choice compounds suitable for the treatment of neoplasias in general as well as of neuroectodermal origin (such as for example neuroblastoma, peripheral primitive neuroectodermal tumour (pPNET), Ewing's sarcoma, melanoma, microcytoma, etc.). That is extremely important, considering that a tumour of neuroectodermal origin, i.e. neuroblastoma, is one of the most common pediatric solid tumours and accounts for 10% of cancers in children, with unfavourable prognosis in 85% of cases, and that 10 new cases/million of melanoma are diagnosed each year in Australia and 10-15 in Europe and in the United States.

To this end, the derivatives according to the present invention may be used in the preparation of pharmaceutical composition, administrable in the form of pharmaceutical formulations commonly used for drug administration by the parenteral and oral routes as well as of formulations for local administration, possibly at the tumour primary and/or secondary site. Furthermore, aloe-emodin derivatives may be used in the preparation of pharmaceutical compositions suitable for the purging in autologous marrow transplant.

For the preparation of the compositions according to the invention it is possible to use all pharmaceutically acceptable excipients, including vehicles or devices for controlled release local administration.

The compositions for the treatment of neoplasias, which contain aloe-emodin derivatives as active ingredients, may especially be formulations with an active ingredient content suitable for obtaining the therapeutic effect according to the purpose of the present invention. In particular, dosages may range e.g. from 5 to 500 mg for unit administration and from 2 to 500 mg for purging.

Said formulations can be prepared according to methods known in the art or according to new pharmaceutical technologies, using pharmaceutically acceptable excipients, diluents, emulsifiers, aqueous or oily or polymeric vehicles, etc., capable of releasing the active ingredient also at a controlled rate, e.g. with fast or sustained or delayed release.

The formulations administrable by the parenteral way may be produced in all classical pharmaceutical forms, such as ampoules in aqueous or oily vehicles, or in buffer solutions or containing adequate suspending agents, or in the form of freeze-dried products to be reconstituted immediately prior to administration.

The formulations for oral administration may be tablets, soft or hard gelatine capsules either oily or operculate, pills, powders for reconstitution, suspensions, and emulsions.

The compositions according to the present invention may also consist of formulations for topical or transdermic use in vehicles or devices suitable for the active ingredient application to the primary or secondary tumour site.

Excipients, binding agents, lubricants, anticaking agents, etc. may be of any type and anyhow suitable for pharmaceutical purposes and adequate to the object of the present invention. By way of example, they may be sugars (e.g. mannitol, lactose, dextrose, saccharose, fructose), natural polysaccharides, such as cellulose and derivatives thereof, e.g. methylcellulose, carboxymethylcellulose, starch and alginates, as well as other polymeric excipients already known and used in the pharmaceutical field, i.e. silica, talc, magnesium oxide, stearates, polyethylene glycols, Arabic gum, polyvinylpyrrolidone and polyvinyl alcohol.

The invention claimed is:

1. Compounds of formula

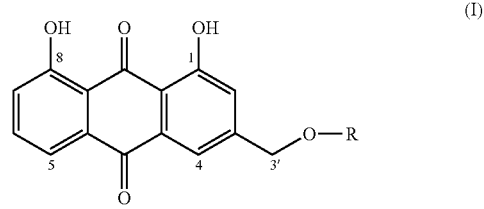

where R can be the radical of:
a saturated or unsaturated $C_2$-$C_6$ linear or branched chain aliphatic polycarboxylic acid, optionally substituted on the aliphatic chain by suitable hydrophilic groups;
an arylic polycarboxylic acid, optionally substituted on the aromatic ring by small hydrophilic residues;
an amino acid;
an acetal of an amino sugar with the proviso that the amino sugar is not glucosamine; or
an inorganic acid.

2. The compounds as claimed in claim 1, wherein said polycarboxylic aliphatic acids are selected from the group consisting of bicarboxylic and tricarboxylic acids, optionally substituted on the aliphatic chain by suitable hydrophilic groups.

3. The compounds as claimed in claim 2, wherein said polycarboxylic aliphatic acids are selected from the group consisting of oxalic, malic, succinic, glutaric, adipic, pimelic, maleic, diglycolic and citric acids.

4. The compounds as claimed in claim 1, wherein said arylic polycarboxylic acids are selected from the group consisting of aromatic systems containing one or two rings optionally substituted with hydrophilic residues, and at least two carboxylic groups.

5. The compounds as claimed in claim 4, wherein said arylic polycarboxylic acids are selected from the group consisting of phthalic acid and 1,2,4-benzenetricarboxylic acid.

6. The compounds as claimed in claim 1, wherein said amino acids are selected from the group consisting of amino acids with the amino group in α- or in other positions.

7. The compounds as claimed in claim 1, wherein said amino sugar is daunosamine.

8. The compounds as claimed in claim 1, wherein said inorganic acid is phosphoric acid.

9. The compounds as claimed in claim 1, wherein the free carboxylic group of the saturated or unsaturated $C_2$-$C_6$ linear or branched chain aliphatic and arylic polycarboxylic acids is salified by pharmaceutically acceptable counterions.

10. The compounds as claimed in claim 9, wherein the counterions are sodium or potassium.

11. The compounds as claimed in claim 1, wherein the free aminic group of the amino acids and the amino sugars is salified by pharmaceutically acceptable anionic groups.

12. The compounds as claimed in claim 11, wherein the anionic groups are selected from the group consisting of acetate, trifluoroacetate, nitrate, chloride, bromide and acid sulphate.

13. A method for the treatment of neoplastic pathologies, which comprises administering to a subject an effective amount of compounds of formula

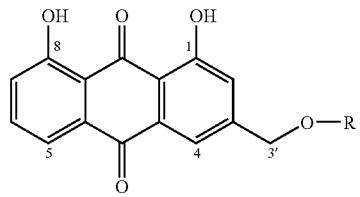

(I)

where R may be the radical of:
a saturated or unsaturated $C_2$-$C_6$ linear or branched chain aliphatic polycarboxylic acid, optionally substituted on the aliphatic chain by suitable hydrophilic groups;
an arylic polycarboxylic acid, optionally substituted on the aromatic ring by small hydrophilic residues;
an amino acid;
an acetal of an amino sugar;
an inorganic acid;
and salts thereof;
said neoplastic pathologies selected from neoplasias of neuroectodermal origin, adenocarcinomas and gliomas.

14. The method as claimed in claim 13, wherein said aliphatic polycarboxylic acids are selected from the group consisting of bicarboxylic and tricarboxylic acids, optionally substituted on the aliphatic chain by suitable hydrophilic groups.

15. The method as claimed in claim 14, wherein said aliphatic polycarboxylic acids are selected from the group consisting of oxalic, malic, succinic, glutaric, adipic, pimelic, maleic, diglycolic and citric acids.

16. The method as claimed in claim 13, wherein said arylic polycarboxylic acids are selected from the group consisting of aromatic systems containing one or two rings optionally substituted with hydrophilic residues, and at least two carboxylic groups.

17. The method as claimed in claim 16, wherein said arylic polycarboxylic acids are selected from the group consisting of phthalic acid and 1,2,4-benzenetricarboxylic acid.

18. The method as claimed in claim 13, wherein said amino acids are selected from the group consisting of amino acids with the amino group in α- or in other positions.

19. The method as claimed in claim 13, wherein said amino sugar is daunosamine.

20. The method as claimed in claim 13, wherein said inorganic acid is phosphoric acid.

21. Pharmaceutical compositions containing, as active ingredient, at least one compound of formula

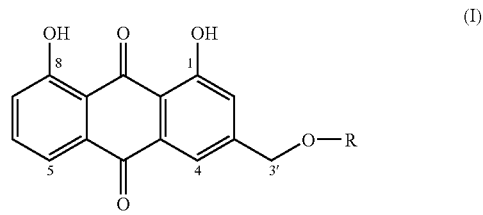

(I)

where R may be the radical of:
a saturated or unsaturated $C_2$-$C_6$ linear or branched aliphatic chain polycarboxylic acid, optionally substituted on the aliphatic chain by suitable hydrophilic groups;
an arylic polycarboxylic acid, optionally substituted on the aromatic ring by small hydrophilic residues;
an amino acid;
an acetal of an amino sugar;
an inorganic acid;
and salts thereof, in combination with pharmaceutically acceptable excipients and/or diluents for therapeutic use, suitable to deliver and release the active ingredient optionally at a controlled rate.

22. The pharmaceutical compositions as claimed in claim 21 suitable for administration by the parenteral, intravenous, subcutaneous, and intramuscular routes.

23. The pharmaceutical compositions as claimed in claim 21 suitable for oral administration in the form of granular powders, tablets, pills, and capsules.

24. The pharmaceutical compositions as claimed in claim 21 suitable for topical and transcutaneous administration.

25. The pharmaceutical compositions as claimed in claim 21 suitable for the purging in autologous marrow transplant.

26. The compounds as claimed in claim 6, wherein said amino acids are selected from the group consisting of alanine, isoleucine, tyrosine, tryptophan and GABA.

27. The methods as claimed in claim 18, wherein said amino acids are selected from the group consisting of alanine, isoleucine, tyrosine, tryptophan and GABA.

* * * * *